(12) United States Patent
Pettinato et al.

(10) Patent No.: US 10,226,228 B2
(45) Date of Patent: Mar. 12, 2019

(54) IMAGING SYSTEM SUBJECT SUPPORT

(71) Applicant: KONINKLIJKE PHILIPS N.V., Eindhoven (NL)

(72) Inventors: Jeremy David Pettinato, Mentor, OH (US); Allan Joseph Sokalski, Mentor, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 834 days.

(21) Appl. No.: 14/401,631

(22) PCT Filed: Jun. 6, 2013

(86) PCT No.: PCT/IB2013/054654
§ 371 (c)(1),
(2) Date: Nov. 17, 2014

(87) PCT Pub. No.: WO2013/186671
PCT Pub. Date: Dec. 19, 2013

(65) Prior Publication Data
US 2015/0141796 A1    May 21, 2015

Related U.S. Application Data

(60) Provisional application No. 61/658,433, filed on Jun. 12, 2012.

(51) Int. Cl.
*A61B 6/03* (2006.01)
*A61B 6/04* (2006.01)
(Continued)

(52) U.S. Cl.
CPC .............. *A61B 8/40* (2013.01); *A61B 5/0555* (2013.01); *A61B 6/035* (2013.01); *A61B 6/04* (2013.01); *A61B 6/0442* (2013.01); *A61B 6/0457* (2013.01)

(58) Field of Classification Search
CPC .... A61G 13/02; G02B 6/4226; G02B 6/4231; F16H 25/2445; F16H 25/2233;
(Continued)

(56) References Cited

U.S. PATENT DOCUMENTS 3,464,283 A * 9/1969 Miller .................... B23Q 5/408
408/241 R
5,014,292 A  5/1991 Siczek et al.
(Continued)

FOREIGN PATENT DOCUMENTS

CN       201328816 Y   10/2009
DE    102004013585 A1  10/2005
(Continued)

*Primary Examiner* — Thomas J Hong
*Assistant Examiner* — Helene Bor

(57) ABSTRACT

A subject support (114) of an imaging system (100) includes a tabletop (124) that supports a subject or object in an examination region of the imaging system, a base (116), including a mechanical linear actuator (118), and a coupling (128) that mechanically couples the tabletop and the linear mechanical actuator such that the linear mechanical actuator translates the tabletop with respect to the examination region. The coupling rotates in two directions and translates in two directions, thereby providing four degrees of freedom, compensating for at least one of machining inaccuracies or misalignment of the linear mechanical actuator.

22 Claims, 6 Drawing Sheets

(51) Int. Cl.
*A61B 8/00* (2006.01)
*A61B 5/055* (2006.01)
(58) Field of Classification Search
CPC ......... A61B 6/035; A61B 6/04; A61B 6/4447;
A61B 5/0555; A61B 8/40; A61B 6/0442;
A61B 6/0457
See application file for complete search history.

(56) References Cited

U.S. PATENT DOCUMENTS

| | | | | |
|---|---|---|---|---|
| 5,689,994 | A * | 11/1997 | Nagai | B23Q 1/25 |
| | | | | 310/80 |
| 6,095,685 | A * | 8/2000 | Tamura | A61B 6/4441 |
| | | | | 378/195 |
| 6,499,159 | B1 * | 12/2002 | Schmitt | A61B 6/04 |
| | | | | 192/84.9 |
| 7,508,913 | B2 | 3/2009 | Boese | |
| 2002/0120986 | A1 * | 9/2002 | Erbel | A61B 6/0421 |
| | | | | 5/601 |
| 2012/0045038 | A1 | 2/2012 | Moyers | |

FOREIGN PATENT DOCUMENTS

| | | |
|---|---|---|
| JP | 10222228 | 8/1998 |
| JP | 2010-131199 | 6/2010 |
| WO | 2005065482 A1 | 7/2005 |

* cited by examiner ically couples the tabletop and the linear mechanical actuator
IMAGING SYSTEM SUBJECT SUPPORT

CROSS REFERENCE TO RELATED APPLICATIONS

This application is a national filing of PCT application Serial No. PCT/IB2013/054654, filed Jun. 6, 2013, published as WO 2013/186671 A2 on Dec. 19, 2013, which claims the benefit of U.S. provisional application Ser. No. 61/658,433 filed Jun. 12, 2012, which is incorporated herein by reference.

The following generally relates to an imaging system subject support configured to support an object or subject in an examination region of the imaging system before, during and/or after scanning the object or subject, and is described with particular application to computed tomography (CT). However, the following is also amenable to other imaging modalities such as positron emission tomography (PET), single photon emission tomography (SPECT), magnetic resonance imaging (MRI), ultrasound (US), X-ray, and/or other imaging modalities, and/or a combination thereof.

A computed tomography (CT) scanner includes a rotating portion rotatably supported by a stationary portion. The rotating portion supports an x-ray tube, which emits radiation that traverses an examination region and an object or a subject therein, and a detector array that detects radiation traversing the examination region and generates a signal indicative of the detected radiation. A subject support supports the object or subject in the examination region before, during and/or after scanning, for example, for loading the object or subject, feeding the object or subject into and removing the object or subject from the examination region, and unloading the object or subject. A reconstructor reconstructs the signal and generates volumetric image data indicative of the portion of the object or subject in the examination region.

The subject support has included a base, which is affixed to the floor of the examination room and is configured to move vertically, under electronic control, with respect to the floor, and a tabletop, which is affixed to the base and is configured to translate horizontally, under electronic control or manually via a user, with respect to the base, in and out of the examination region before, during and/or after scanning. The tabletop has been moveably affixed to the base through linear slide bearings and a mechanical linear actuator, such as a leadscrew, which includes a threaded shaft mounted to the base and a complementary threaded nut affixed to the tabletop. The threaded shaft rotates which provides a helical raceway for the nut, which translates along the threaded shaft. Rotating the threaded shaft causes the nut to linearly translate along the axis of the threaded shaft and hence the table top to linearly translate along the slides.

Generally, the threaded shaft requires tight machining and/or alignment tolerances as machining inaccuracies and/or misalignment can cause undesired horizontal flow force, which inhibits the nut from translating along the threaded screw. Undesired horizontal flow force may lead to imaging system downtime (e.g., to replace or re-align the screw) and having to re-schedule patients for another day and/or with another imaging system. Tight machining and/or alignment tolerances may increase manufacturing build time and/or overall system cost. In one system, the nut is attached to a coupling that provides two degrees of freedom, which has been enough to compensate for machining inaccuracies and/or misalignment and undesired horizontal flow force, and the additional cost of more elaborate systems has not been warranted.

Aspects described herein address the above-referenced problems and others.

In one aspect, a subject support of an imaging system includes a tabletop that supports a subject or object in an examination region of the imaging system, a base, including a linear mechanical actuator, and a coupling that mechanically couples the tabletop and the linear mechanical actuator such that the linear mechanical actuator translates the tabletop with respect to the examination region. The coupling rotates in two directions and translates in two directions, thereby providing four degrees of freedom, compensating for at least one of machining inaccuracies or misalignment of the linear mechanical actuator.

In another aspect, a method includes translating a tabletop of a subject support of an imaging system with respect to a base of the subject support via a coupling and a linear mechanical actuator, wherein the coupling is attached to the tabletop and a linear mechanical actuator, which is attached to the base, and wherein the coupling provides four degrees of freedom for the linear mechanical actuator.

In another aspect, an imaging system includes a radiation source that emits radiation that traverses an examination region, a radiation sensitive detector array that detects radiation that traverses the examination region, and a subject support that supports a subject or object in the examination region. The subject support includes a tabletop that supports a subject or object in an examination region of the imaging system, a base, including a linear mechanical actuator, and a coupling that mechanically couples the tabletop and the linear mechanical actuator, which translates the tabletop with respect to the examination region. The coupling rotates in two opposing directions and translates in two opposing directions, thereby compensating for at least one of machining inaccuracies or misalignment of the linear mechanical actuator.

The invention may take form in various components and arrangements of components, and in various steps and arrangements of steps. The drawings are only for purposes of illustrating the preferred embodiments and are not to be construed as limiting the invention.

FIG. 1 schematically illustrates an imaging system including a subject support.

Figure 1:
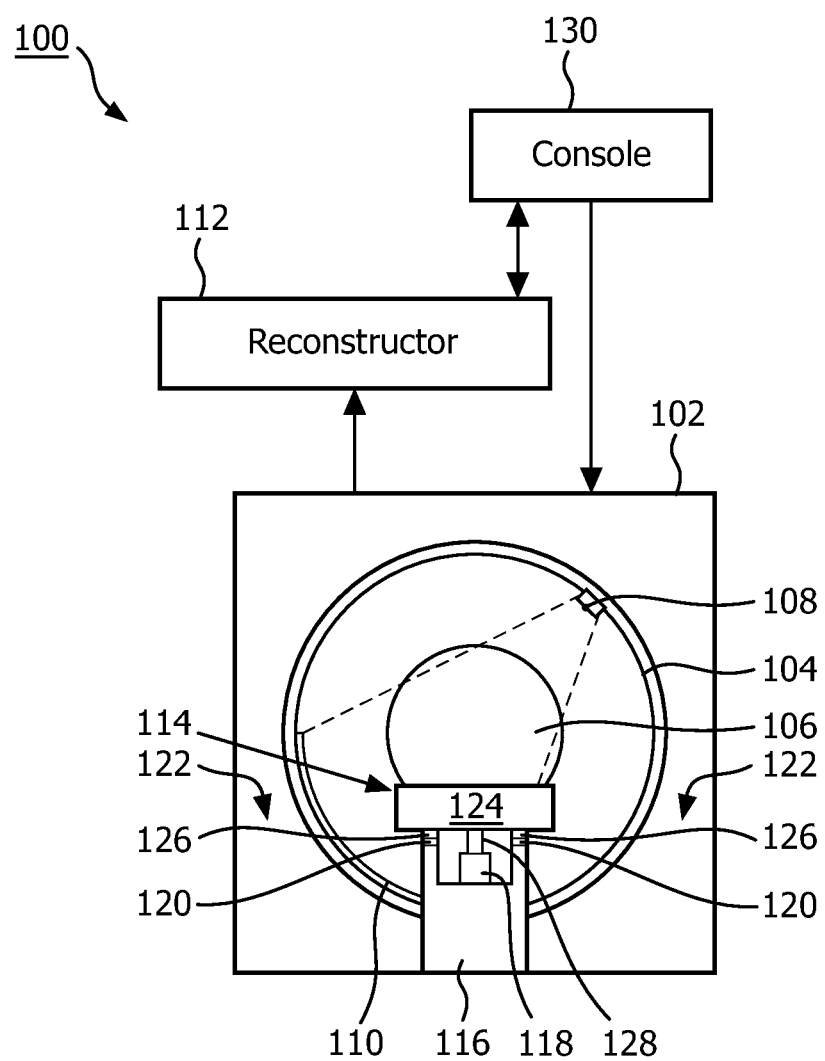

FIG. 1 schematically illustrates an imaging system 100. The imaging system 100 can be a CT, PET, SPECT, MRI, US, X-ray, a combination thereof (e.g., CT/PET, etc.), and/or other imaging modality imaging system. However, for sake of brevity and clarity, the following will be described in relation to a CT scanner.

The illustrated imaging system 100 includes a generally stationary gantry 102 and a rotating gantry 104, which is rotatably supported by the stationary gantry 102 and rotates around an examination region 106 about a z-axis. A radiation source 108, such as an x-ray tube, is rotatably supported by the rotating gantry 104, rotates with the rotating gantry 104, and emits radiation that traverses the examination region 106. A radiation sensitive detector array 110 subtends an angular arc opposite the radiation source 108 across the examination region 106. The radiation sensitive detector array 110 detects radiation traversing the examination region 106 and generates a signal indicative thereof.

A subject support 114, such as a patient couch, supports an object or subject in the examination region 106 before, during and/or after scanning. The illustrated subject support 114 includes a base 116, a mechanical linear actuator 118 affixed to the base 116, first portions 120 of one or more bearings 122 (two shown in this example) affixed to the base 116, a tabletop 124, second portions 126 of the one or more bearings 122 affixed to the tabletop 124, and a coupling 128, which couples the tabletop 124 and the mechanical linear actuator 118. The base 116 affixes to or rests on a floor in an examination room. The mechanical linear actuator 118 translates the coupling 128 and hence the tabletop 124 in a longitudinal or z-direction into and out of the examination region.

As described in greater detail below, the coupling 128 mitigates for machining inaccuracies and/or misalignment of at least the mechanical linear actuator 118 by allowing a portion of the coupling 128 to move (e.g., translate and rotate) with at least three degrees of freedom to compensate for the machining inaccuracies and/or misalignment, thereby, mitigating undesired horizontal flow force and allowing the tabletop to freely translate without undue force. In one instance, this may reduce imaging system downtime to replace or re-align the mechanical linear actuator 118. This may also reduce manufacturing build time, allow for a common force measurement across subject supports and/or subject support product lines, allow for relaxed machining tolerances, etc. At least the above can be achieved while providing a stiff assembly with backlash in a range of 0.50 mm or less, such as 0.25 mm or less and/or at least matching a performance of a configuration of the subject support 114 in which the coupling 128 is not used.

A reconstructor 112 reconstructs the signal, generating volumetric image data indicative of a scanned portion of a subject or object located in the examination region 106. A general-purpose computing system or computer serves as an operator console 130. The console 130 includes a human readable output device such as a monitor and an input device such as a keyboard, mouse, etc. Software resident on the console 130 allows the operator to interact with and/or operate the scanner 100 via a graphical user interface (GUI) or otherwise. In addition, the software instructs the subject support 114 to translate the tabletop 124 to position the subject and/or object for loading and/or unloading, and/or positioning the subject or object before, during and/or after a scan, etc.

Figure 2:
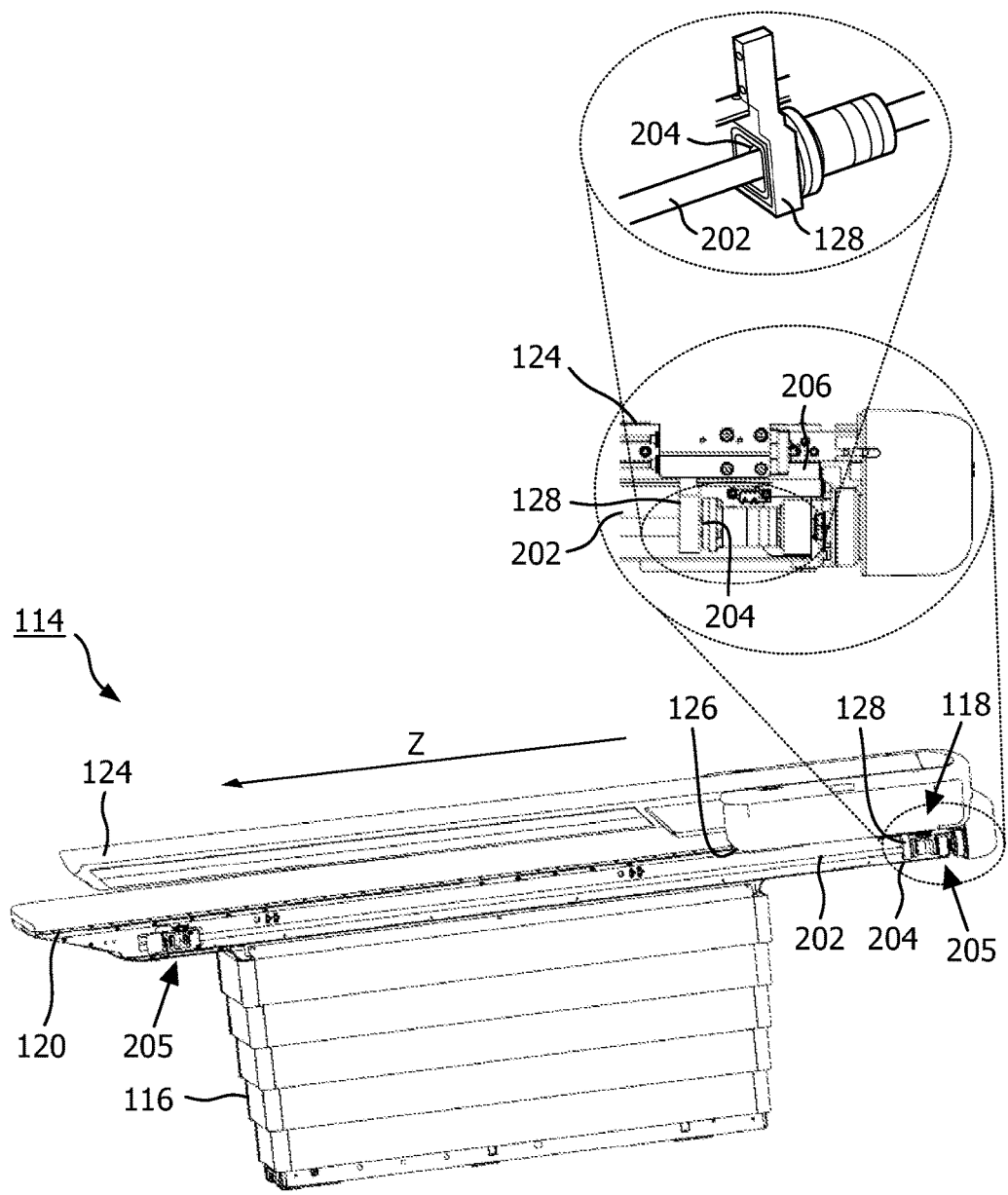
FIG. 2 illustrates an example of the subject support.

FIG. 2 shows a side view of the subject support 114, including an example of the mechanical linear actuator 118. In this example, the mechanical linear actuator 118 includes an elongate threaded shaft 202 and a complementary threaded nut (bolt, or the like) 204. (Note that a ball screw assembly can be alternatively used). The shaft 202 is affixed to the base 116 at ends 205 of the shaft 202 and extends along the z-axis direction.

A motor 206 is operatively coupled to the shaft 202 and rotates the shaft 202. A controller (not visible) drives the motor 206. The coupling 128 fixedly attaches to the tabletop 124 and to the threaded shaft 202 and, hence, couples the tabletop 124 and the mechanical linear actuator 118. Rotating the threaded shaft 202 translates the nut 204 along the z-direction, which translates the tabletop 124 along the z-direction.

Figure 3:
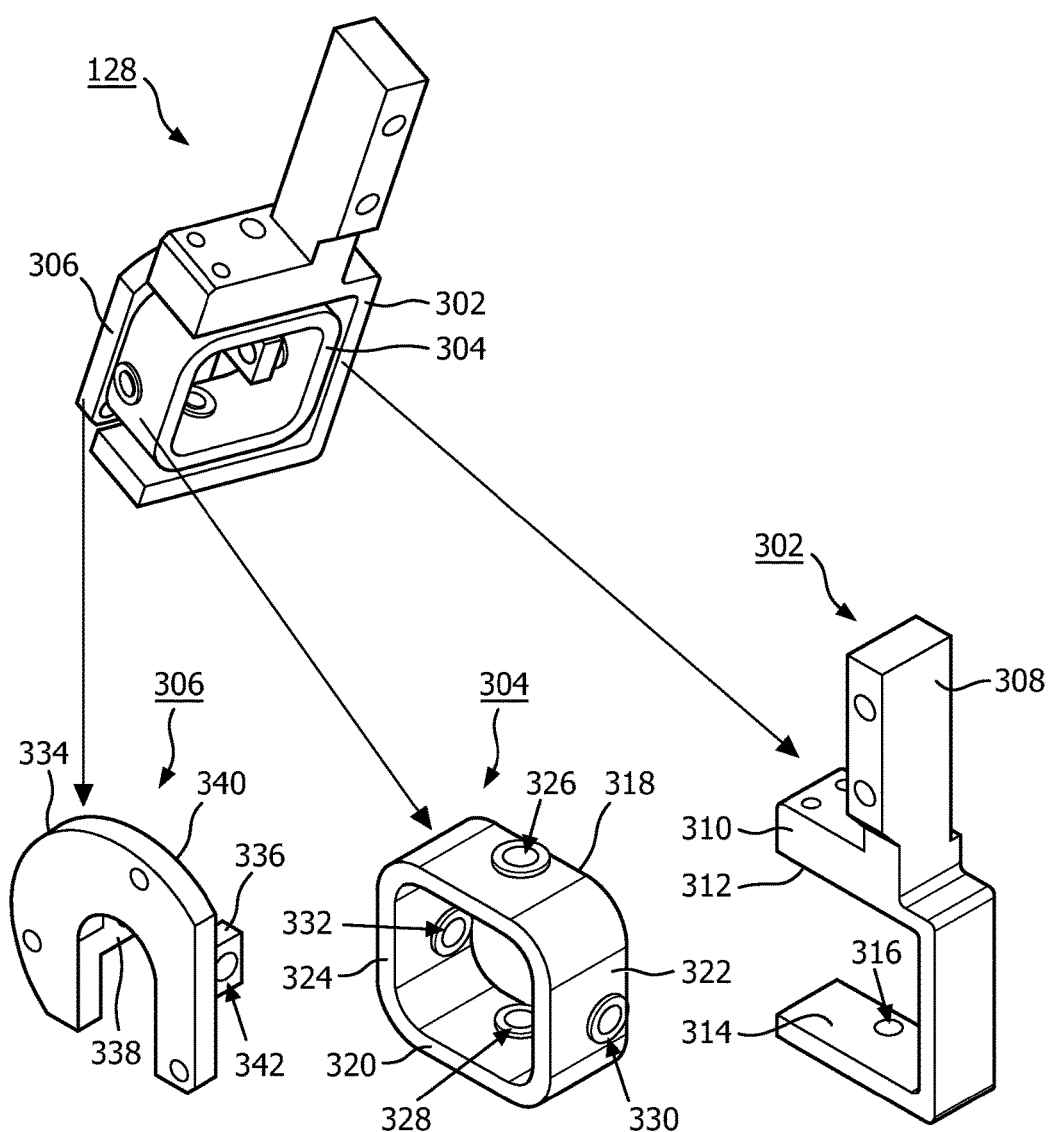
FIGS. 3, 4, 5 and 6 illustrate an example of a coupling of the subject support.
Figure 4:
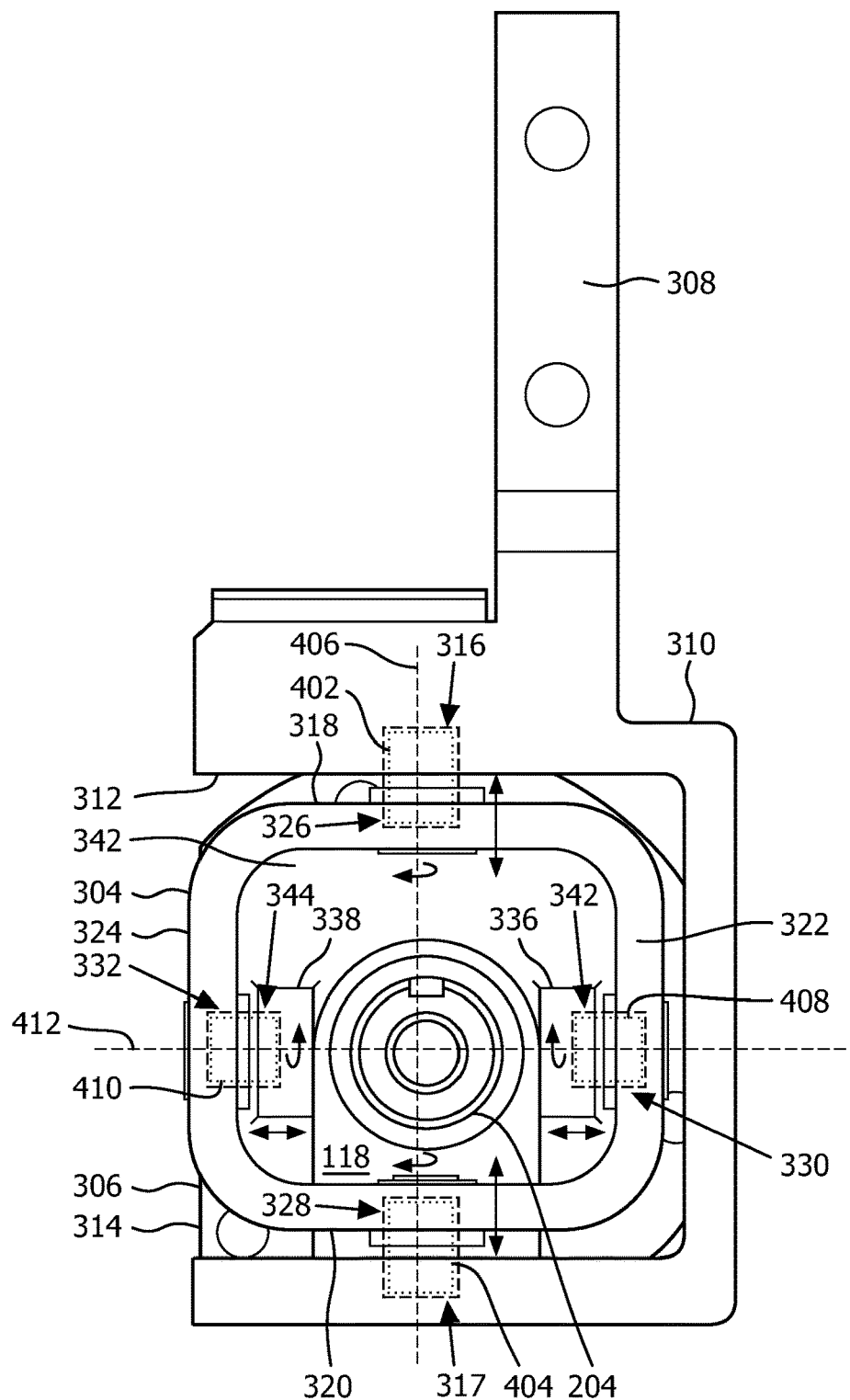
Figure 5:
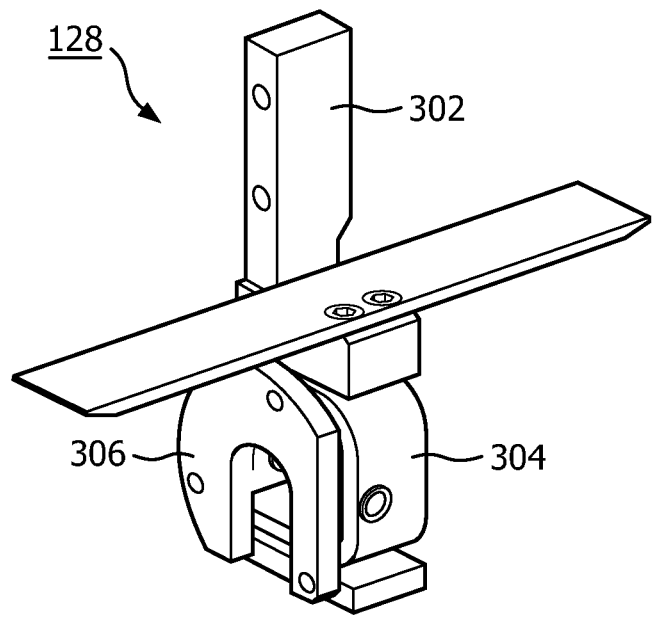
Figure 6:
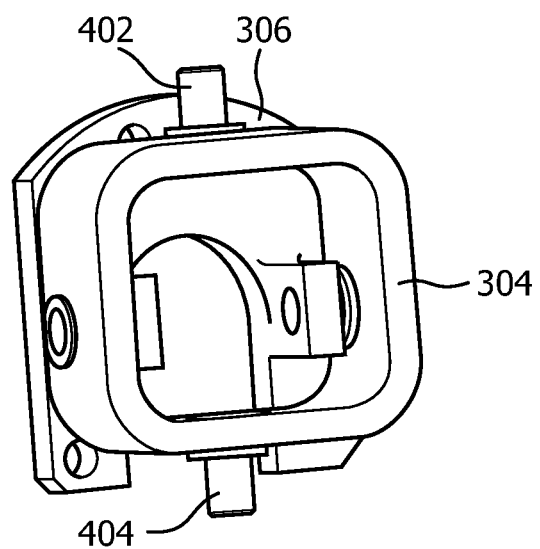

FIGS. 3, 4, 5 and 6 show a non-limiting example of the coupling 128. The illustrated coupling 128 includes a stationary frame 302, a first moveable member 304, and a second moveable member 306. FIG. 3 shows a perspective and exploded view, FIG. 5 shows a perspective view from behind FIG. 3, FIG. 4 shows a front view, and FIG. 6 shows partial view.

The stationary frame 302 includes a tabletop connector 308, which attaches to the tabletop 124 (FIGS. 1 and 2). The stationary frame 302 also includes a body 310 that supports the first moveable member 304. In the illustrated embodiment, the body 310 is "C" shaped in that it includes at least two opposing sides 312 and 314, which face each other. In other embodiments, the body 310 can be circular, rectangular, octagonal, and/or otherwise shaped. At least one of the sides 312 and 314 includes a material free recess 316 and 317.

The first moveable member 304 is "0" shaped in that it includes a first pair of opposing sides 318 and 320 and a second pair of opposing sides 322 and 324, which are generally perpendicular to the first pair. Similar to the stationary frame 302, other shapes are also contemplated herein. At least one of the sides 318 and 320 includes a material free recess 326 and 328, and at least one of the sides 322 and 324 includes a material free recess 330 and 332.

The second moveable member 306 includes a bracket 334 with two protrusions 336 and 338 extending from a major surface 340 of the bracket 334. Similar to the stationary frame 302 and the first moveable member 304, other shapes are also contemplated herein. At least one of the protrusions 336 and 338 includes a material free recess 342 and 344. In FIG. 4, the second moveable member 306 is mounted to the nut 204 of the mechanical linear actuator 118.

The first moveable member 304 is moveably supported by the body 310. As shown in FIG. 4, in one instance, this can be achieved through bearings 402 and 404, which, respectfully, extend into recesses 316 and 326 and recesses 328 and 317. As shown in FIG. 4, the first moveable member 304 rotates about an axis 406 extending between the bearings 402 and 404 and translates along the axis 406. Although the first movable member 304 is shown rotating in one direction, it is to be understood that it rotates or pivots back and forth about the axis 406.

In one instance, the bearings 402 and 404 are fixedly attached to the first moveable member 304 and translate and rotate within the recesses 316 and 317 of the body 310. In another instance, the bearings 402 and 404 are fixedly attached to the body 310 and translate and rotate within the recesses 326 and 328 of the first moveable member 304. In yet another instance, the bearings 402 and 404 are free within all of the recesses 316, 317, 326, and 328.

FIG. 6 shows the bearings 402 and 404 installed in the first moveable member 304 with the stationary frame 302 omitted for explanatory purposes.

The second moveable member 306 is moveably supported by the first moveable member 304. As shown in FIG. 4, in one instance, this can be achieved through bearings 408 and 410, which, respectfully, extend into recesses 330 and 342 and recesses 332 and 344. As shown in FIG. 4, the second moveable member 306 rotates about an axis 412 extending between the bearings 408 and 410 and translates along the axis 412. Note that the rotation and translation are perpendicular to that of the first moveable member 304.

In one instance, the bearings 408 and 410 are fixedly attached to the second moveable member 306 and translate and rotate within the recesses 342 and 344 of the second moveable member 306. In another instance, the bearings 408 and 410 are fixedly attached to the second moveable member 306 and translate and rotate within the recesses 330 and 332 of the first moveable member 304. In yet another instance, the bearings 408 and 410 are free within all of the recesses 330, 332, 342, and 344.

The combination of the translational and rotational movement of the first and second moveable member 304 and 306 with respect to the body 310, as described herein, provides four degrees of freedom and allows the nut, via the coupling 128, to move up, down, left, right and/or diagonal, while translating along the elongate threaded shaft 202, with any machining inaccuracies and/or misalignment of the elongate threaded shaft 202.

At the same time, the coupling 128 decouples the machining inaccuracies and/or misalignment of the elongate threaded shaft 202 from the tabletop 124. In one instance, the above mitigates undesired horizontal flow force of the tabletop 124 caused by not allowing the complementary threaded element 204 to move as such and/or allowing machining inaccuracies and/or misalignment of the elongate threaded shaft 202 to transfer to the tabletop 124.

The coupling 128 also mitigates undesired affects resulting from undesired horizontal flow force of the tabletop 124. For example, the coupling 128 mitigates imaging system downtime from undesired horizontal flow force and having to re-schedule patients due to downtime. In addition, the coupling 128 allows for relaxing machining tolerances (e.g., since machining inaccuracies can be compensated for), which may reduce build time and/or overall system cost. Furthermore, a common horizontal flow force can be maintained across subject supports and/or subject support product lines, unlike configurations in which the coupling 128 is omitted.

Variations are contemplated next.

FIG. 4 shows a four bearing (402, 404, 408 and 410) configuration. In variation, a single bearing could be used for each of the translational and/or rotational motions. In another variation, more than four bearings can be used. In yet another variation, the pairs of bearings are not perpendicular to each other. In still another variation, at least one of the pairs of bearings is positioned at an angle with respect to the axes 406 and 412. In yet another variation, the coupling 128 may include one or more other moveable members. In still another variation, one or more of the recesses may be a slot, which allows a bearing to slide along the long axis of the slot.

Although the embodiments described above show a single linear mechanical actuator, one of ordinary skill in the art would appreciate a variation in which two or more linear mechanical actuators are used. For example, FIG. 2 shows a single linear mechanical actuator located at one side of the subject support 114. In a variation, second linear mechanical actuator can be located on the other side of the subject support 114. FIG. 1 shows a single linear mechanical actuator located along the middle of the subject support 114. In a variation, a second linear mechanical actuator can be located on one or the other sides, an additional linear mechanical actuator can be located at each side of the subject support 114, two linear mechanical actuators can located about the middle, etc.

In another variation, only three degrees of freedom are provided. For example, in one instance, the coupling 128 allow for the two rotational movements, but only one of the translational movements. In one instance, the coupling 128 allow for the two translational movements, but only one of the rotational movements. In yet another variation, the coupling 128 provides more than four degrees of freedom.

Figure 7:
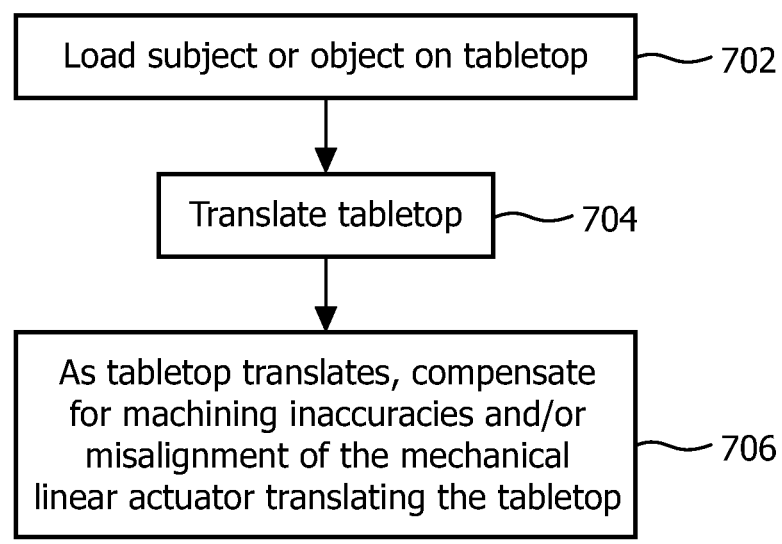
FIG. 7 illustrates a method.

FIG. 7 illustrates an example method.

It is to be appreciated that the ordering of the acts is not limiting. As such, other orderings are contemplated herein. In addition, one or more acts may be omitted and/or one or more additional acts may be included.

At 702, a subject or object is loaded on to a tabletop of a subject support of an imaging system.

At 704, the tabletop is activated to translate along a base of the subject support to position and subject or object in an examination region of the imaging system.

At 706, as the tabletop translates, a coupling that couples the tabletop to a linear mechanical actuator mounted to the base of the subject support compensates for machining inaccuracies and/or misalignment of the mechanical linear actuator.

As described herein, this can be achieved through a configuration of the coupling which allows three or more degrees of freedom to the nut of the mechanical linear actuator so that the nut can translates and/or rotate along with the machining inaccuracies and/or misalignment.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A subject support of an imaging system, comprising:
   a tabletop that supports a subject or object in an examination region of the imaging system;
   a base, including a linear mechanical actuator; and
   a coupling that directly mechanically couples the tabletop and the linear mechanical actuator such that the linear mechanical actuator translates the tabletop with respect to the examination region,
   wherein the coupling rotates in two directions and translates in at least one direction or rotates in at least one direction and translates in two directions, thereby providing at least three degrees of freedom, compensating for at least one of machining inaccuracies or misalignment of the linear mechanical actuator.

2. The subject support of claim 1, wherein the coupling rotates in the two directions and translates in the two directions.

3. The subject support of claim 1, wherein the linear mechanical actuator includes a threaded screw and a complementary threaded nut, the screw is affixed to the base, the nut is affixed to the coupling, which is affixed to the tabletop, and the nut translates along the screw in response to controlled rotational motion of the screw, thereby translating the tabletop.

4. The subject support of claim 3, the coupling, comprising:
   a first moveable member:
   a second moveable member that attaches to the threaded nut, wherein the first moveable member rotatably and translatably supports the second moveable member; and
   a stationary frame, including:
      a tabletop connector that attaches to the tabletop; and
      a body, wherein the body rotatably and translatably supports the first moveable member.

5. The subject support of claim 4, wherein the first moveable member translates in a first linear direction and the second moveable member translates in a second linear direction, and the first and second linear directions are perpendicular to each other.

6. The subject support of claim 5, further comprising:
at least one bearing, wherein the first moveable member is coupled to the body via the at least one bearing, and the first moveable member translates via the at least one bearing.

7. The subject support of claim 6, wherein the body includes at least two opposing sides with respective recesses, the first moveable member includes at least two opposing sides with respective recesses, the at least one bearing includes two bearings, and one of the bearings extends into one of the recesses of the sides of the body and one of the recesses of the sides of the first moveable member and the other of the bearings extends into the other of the recesses of the sides of the body and the other of the recesses of the sides of the first moveable member.

8. The subject support of claim 4, wherein the first moveable member rotates in a first rotational direction and the second moveable member rotates in a second rotational direction, and the first and second rotational directions are perpendicular to each other.

9. The subject support of claim 8, further comprising:
at least a second bearing, wherein the second moveable member is coupled to the first moveable member via the at least one second bearing, and the second moveable member rotates via the at least one second bearing.

10. The subject support of claim 9, wherein the body includes a second pair of at least two opposing sides with respective recesses, the second moveable member includes at least two protrusions with respective recesses, the at least one bearing includes two bearings, and one of the bearings extends into one of the recesses of the sides of the body and one of the recesses of the sides of the protrusions and the other of the bearings extends into the other of the recesses of the sides of the body and the other of the recesses of the sides of the protrusions.

11. The subject support of claim 1, wherein the subject support includes only a single linear mechanical actuator located at a side or a middle region of the subject support.

12. The subject support of claim 1, wherein the subject support includes two or more linear mechanical actuators and corresponding couplings.

13. The subject support of claim 1, wherein the coupling decouples the machining inaccuracies and/or misalignment of the linear mechanical actuator from the tabletop.

14. The subject support of claim 1, further comprising:
a linear slide bearing, wherein the tabletop translates with respect to the base via the linear slide bearing.

15. A method, comprising:
translating a tabletop of a subject support of an imaging system with respect to a base of the subject support via a coupling and a linear mechanical actuator, wherein the coupling is attached to the tabletop and the linear mechanical actuator, which is directly attached to the base, and wherein the coupling provides four degrees of freedom for the linear mechanical actuator.

16. The method of claim 15, wherein the coupling decouples the machining inaccuracies and/or misalignment of the linear mechanical actuator from the tabletop.

17. The method of claim 15, wherein the coupling is attached to a threaded nut of the linear mechanical actuator that is configured to translate along an elongate threaded shaft of the linear mechanical actuator attached to the base, and further comprising:
rotating the elongate threaded screw, thereby translating the nut, translating the coupling, and translating the tabletop.

18. The method of claim 17, further compromising:
allowing, via the coupling, the threaded nut to translate at least one of up, down, left, or right, with respect to the elongate threaded screw, as the threaded nut translates along the elongate threaded screw.

19. The method of claim 17, further compromising:
allowing, via the coupling, the threaded nut to rotate in at least two axes which are perpendicular to each other, as the threaded nut translates along the elongate threaded screw.

20. An imaging system, comprising:
a radiation source that emits radiation that traverses an examination region;
a radiation sensitive detector array that detects radiation that traverses the examination region and produces a signal indicative thereof;
a reconstructor configured to reconstruct the signal, thereby generating image data; and
a subject support that supports a subject or object in the examination region, the subject support, including:
a tabletop that supports a subject or object in an examination region of the imaging system;
a base, including a linear mechanical actuator; and
a coupling that directly mechanically couples the tabletop and the linear mechanical actuator, which translates the tabletop with respect to the examination region,
wherein the coupling rotates in two opposing directions and translates in two opposing directions, thereby compensating for at least one of machining inaccuracies or misalignment of the linear mechanical actuator.

21. The imaging system of claim 20, wherein the linear mechanical actuator includes a threaded screw and a complementary threaded nut, the screw is affixed to the base, the nut is affixed to the coupling, which is affixed to the tabletop, and the nut translates along the screw in response to controlled rotational motion of the screw, thereby translating the tabletop.

22. The imaging system of claim 21, the coupling, comprising:
a first moveable member:
a second moveable member that attaches to the threaded nut, wherein and the first moveable member rotatably and translatably supports the second moveable member via a first set of bearings; and
a stationary frame, including:
a tabletop connector that attaches to the tabletop; and
a body, wherein the body rotatably and translatably supports the first moveable member via a second set of bearings.

* * * * *